United States Patent [19]

Kolobow

[11] Patent Number: 5,255,675
[45] Date of Patent: Oct. 26, 1993

[54] DEVICE FOR INTRATRACHEAL VENTILATION AND INTRATRACHEAL PULMONARY VENTILATION

[75] Inventor: Theodor Kolobow, Rockville, Md.

[73] Assignee: The United States of America as represented by the Secretary of the Department of Health and Human Services, Washington, D.C.

[21] Appl. No.: 606,967

[22] Filed: Oct. 31, 1990

[51] Int. Cl.⁵ .................... A61M 16/00; A62B 7/00; A62B 9/06; F15C 1/08
[52] U.S. Cl. ........................ 128/204.18; 128/204.25; 128/204.24; 128/207.14
[58] Field of Search .................. 128/207.14, 207.15, 128/207.16, 207.17, 207.29, 200.26, 204.18, 204.24, 204.25; 604/172, 264, 265, 281

[56] References Cited

U.S. PATENT DOCUMENTS

| | | | |
|---|---|---|---|
| 3,460,541 | 8/1969 | Doherty | 128/207.14 |
| 3,538,918 | 11/1970 | Engelsher et al. | 128/200.26 |
| 3,682,166 | 8/1972 | Jacobs | 128/205.19 |
| 3,788,326 | 1/1974 | Jacobs | 128/207.14 |
| 4,082,093 | 4/1978 | Fry et al. | 128/205.24 |
| 4,141,356 | 2/1979 | Smargiassi | 128/205.24 |
| 4,202,330 | 5/1980 | Jariabka | 128/204.18 |
| 4,224,939 | 9/1980 | Lang | 128/205.13 |
| 4,232,667 | 11/1980 | Chalon et al. | 128/203.26 |
| 4,421,113 | 12/1983 | Gedeon et al. | 128/204.23 |
| 4,502,482 | 3/1985 | DeLuccia et al. | 128/207.15 |
| 4,508,117 | 4/1985 | Rodari | 128/204.21 |
| 4,519,388 | 5/1985 | Schwanbom et al. | 128/207.15 |
| 4,593,690 | 6/1986 | Sheridan et al. | 128/207.15 |
| 4,682,010 | 7/1987 | Drapeau et al. | 128/204.17 |
| 4,716,896 | 1/1988 | Ackerman | 128/200.26 |
| 4,773,411 | 9/1988 | Downs | 128/204.18 |
| 4,850,349 | 7/1989 | Farahany | 128/207.15 |
| 4,892,095 | 1/1990 | Nakhgevany | 128/207.14 |
| 4,996,980 | 3/1991 | Frankenberger et al. | 128/200.24 |
| 5,072,726 | 12/1991 | Mazloomdoost et al. | 128/203.12 |

FOREIGN PATENT DOCUMENTS

| | | | |
|---|---|---|---|
| 8801323 | 12/1989 | Netherlands | 128/204.21 |
| 2137506 | 10/1984 | United Kingdom | 128/207.14 |
| 8902761 | 4/1989 | World Int. Prop. O. | 128/207.14 |

OTHER PUBLICATIONS

McPherson, "Respiratory Therapy Equipment", 2nd ed, ®1981, C. V. Mosby Co., St. Louis, Mo., ISBN 080163313-3, pp. 216–220, 229, 230, 309–322, 513.
Cress et al, "A Clinical Guide To Cardiopulmonary Medicine", Puritan-Bennett Corp., 1989, Kansas City, Mo.
"Elective Percutaneous . . . ", Ciaglia et al, Chest/87/6/Jun. 1985, pp. 715–719.
"Respiratory Rehabilitation . . . ", Heimlich, Annals of Otology, Rhinology . . . , Nov./Dec. 1982, vol. 91, #6, pp. 643–647.
"Isothermal TM", Baxter, 12 pp., ®1987, Baxter, Valencia, Calif, 91355 & Isothermal Systems, Inc., Riverside, Calif., 92507.
"Inspiratory Work . . . ", Katz et al, Chest/88/4/Oct. 1985.

Primary Examiner—Edgar S. Burr
Assistant Examiner—Kimberly L. Asher
Attorney, Agent, or Firm—Lowe, Price, LeBlanc & Becker

[57] ABSTRACT

A method and apparatus for intratracheal ventilation (ITV) and intratracheal pulmonary ventilation (ITPV) in which a catheter positioned in a patient's trachea at the carina supplies a constant supply of fresh oxygen containing gas to flush anatomical dead space. By positioning the catheter in the patient's trachea, the dead space of the trachea is bypassed and the trachea is only utilized for expiration. By providing a timed expiratory valve in the ITPV mode, lower pressures and fresh oxygen flow rates may be utilized with respiratory rates from 10 to 120 breaths per minute or higher. The catheter has a diffuser tip, and the patient is ventilated at a flow rate between 0.54 to 4 times the anatomical dead space per breath.

13 Claims, 2 Drawing Sheets

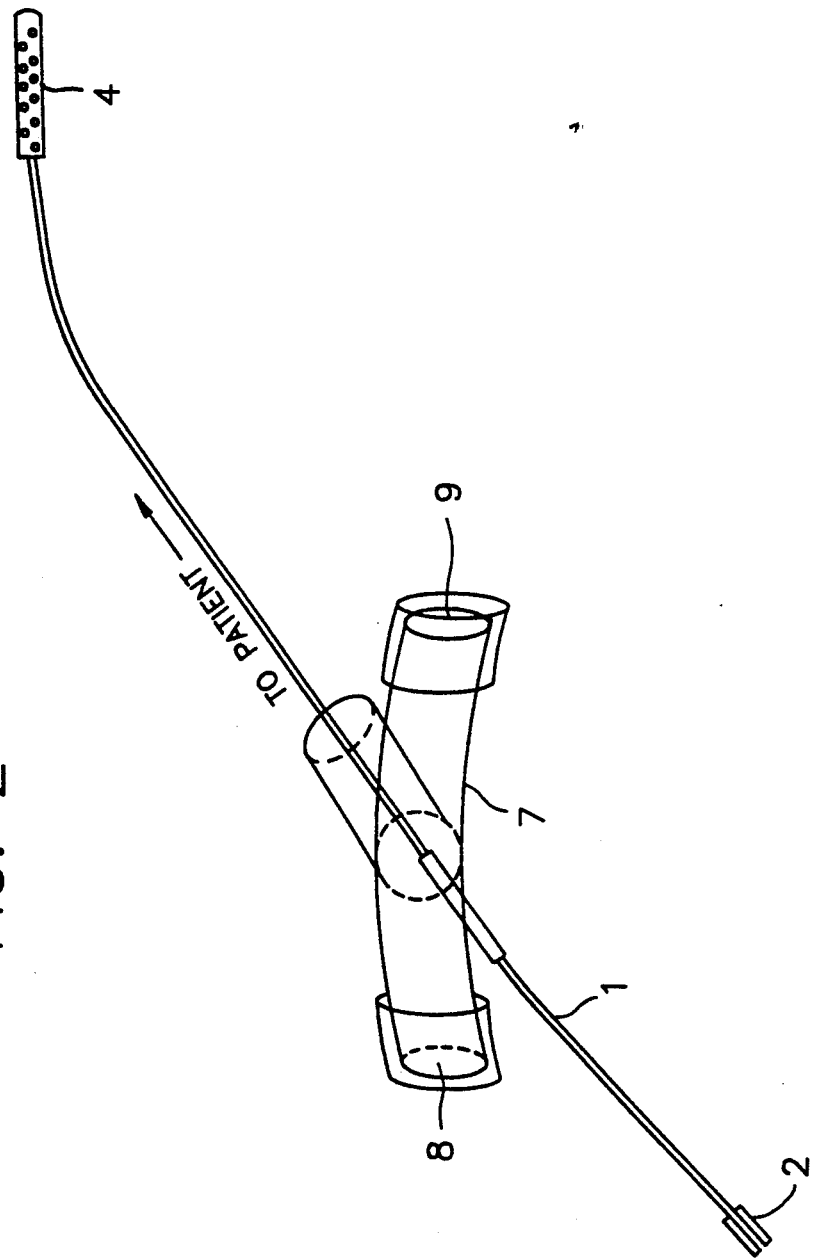

DEVICE FOR INTRATRACHEAL VENTILATION AND INTRATRACHEAL PULMONARY VENTILATION

TECHNICAL FIELD

The present invention relates to intratracheal ventilation and intratracheal pulmonary ventilation methods and apparatus. More particularly, the present invention relates to methods and devices for intratracheal ventilation and intratracheal pulmonary ventilation.

BACKGROUND ART

Congenital diaphragmatic hernia (CDH) currently carries a mortality in excess of 50 percent. Presently, there exists a need for a reliable procedure for providing the necessary ventilation treatment for patients suffering from CDH.

Recent laboratory and clinical evidence strongly implicates mechanical ventilation (MV) at high peak inspiratory pressure (PIP) in the emergence of respiratory distress syndrome (RDS) in the neonate, child and adult. Recovery from severe lung injury is oftentimes facilitated through the use of extracorporeal membrane oxygenation (ECMO), or extracorporeal carbon dioxide removal ($ECCO_2R$), while airway pressures are markedly reduced (lung rest); here, the bulk of $CO_2$ is removed by the extracorporeal membrane lung (ML), allowing lower tidal volumes (VT), respiratory rates (RR), and PIP. Such lung rest cannot be attained only with the use of an extracorporeal ML.

Conventional mechanical pulmonary ventilation as presently utilized is not considered effective at very high respiratory rates, in part because of unavoidable dead space ventilation.

The effect of the anatomical dead space on $CO_2$ removal has been well recognized. In the adult and child, MV (or spontaneous breathing) at frequencies in excess of 60 breaths per minute is oftentimes not effective.

Although work has been made in the field of pulmonary ventilation, there remains a need for a method and apparatus which allows for respiratory rates which are well below what is presently considered practical.

U.S. Pat. No. 4,082,093 to Fry et al discloses the use of a compensator valve for use with a ventilation system. A positive end expiratory pressure (PEEP) valve is also furnished to maintain an artificial residual pressure in the lungs. The magnitude of PEEP may be varied from cycle to cycle. The compensator valve functions to hold the lung pressure constant at the end of the expiratory cycle.

U.S. Pat. No. 4,141,356 to Smargiassi discloses a respiratory system with both assisted and spontaneous modes of breathing. A control circuit responds to the patient's breathing pattern to alter the system between the two modes, in accordance with a predetermined pattern. As illustrated in FIG. 1, the system also includes regulators 10 and 12 which are used to feed a mixture of both air and oxygen.

U.S. Pat. No. 4,202,330 to Jariabka discloses a small tube 13 which is inserted into the trachea for administering oxygen. The tube is connected to a conduit 20 which is connected at 31 to a valving means 30. A second conduit 40 is connected to the inlet 32 of the valve and the other end of the conduit is connected to an oxygen supply 50 which supplies oxygen at a low temperature.

U.S. Pat. No. 4,224,939 to Lang discloses a pulmonary ventilation system in which a respirator feeds air at a controllable pressure, volume, rate, and respiratory frequency to a humidifier. The humidifier is supplied with sterile, heated water. Tube sections 9 and 12 which supply the conditioned air to an endotracheal tube are connected to an inflatable bag 10 by tee 11.

U.S. Pat. No. 4,232,667 to Chalon et al discloses a ventilating system in which both oxygen and an anaesthetic are controllably passed by a flow meter through an inspiratory limb 16 and a small endotracheal tube which is positioned at the approximate level of the carina. An expiratory limb 18 surrounds the inspiratory limb 16. The expiratory limb is connected to an expiratory valve 34. The limbs are provided with spacing ribs 20 to prevent kinking.

U.S. Pat. No. 4,421,113 to Gedeon et al discloses a lung ventilator for carrying out mandatory minute volume (MMV) treatment. The breathing gas source delivers a volume of gas which is at least equal to the maximum volume that may be required. An inspiratory line is connected to the patient's airway for spontaneous breathing. A ventilator is connected to the breathing gas source and is actuated by a signal to deliver a mandatory breath of a predetermined tidal volume to the patient.

U.S. Pat. No. 4,773,411 to Downs discloses a respiratory method and apparatus which establishes a continuous positive airway pressure (CPAP) to enhance functional residual capacity (FRC). Instead of imposing cycles of elevated airway pressure above a CPAP, airway pressure release ventilation (APRV) is utilized to achieve augmentation of alveolar ventilation and carbon dioxide excretion through intermittent cycles of reduced airway pressure below the CPAP pressure level. Breathing gas may be supplied by a variety of devices including a tight fitting tracheal tube.

U.S. Pat. No. 4,593,690 to Sheridan et al discloses an endotracheal tube having an inflatable balloon cuff which is designed so a to be bendable in various directions.

U.S. Pat. No. 4,716,896 to Ackerman discloses an endotracheal tube 40 which is inserted through the mouth of a patient. Within the endotracheal tube is a catheter 10 which delivers a fluid. The catheter has apertures 18a and 18b at its distal end. The catheter may be made of various plastic materials.

U.S. Pat. No. 4,892,095 to Nakhgevany discloses an endotracheal tube having a diffuser 22 at its end.

The present invention is an improvement over existing methods and apparatus utilized in pulmonary ventilation.

DISCLOSURE OF THE INVENTION

It is according one object of the present invention to provide a method of ventilatory assistance to a patient.

Another object of the present invention is to provide a method of intratracheal ventilation and intratracheal pulmonary ventilation.

A further object of the present invention is to provide a method of intratracheal and intratracheal pulmonary ventilation which allows for low peak airway pressures and respiratory rates well beyond what is presently considered practical.

A still further object of the present invention is to provide an apparatus for intratracheal and intratracheal pulmonary ventilation which allows for low peak airway pressures and respiratory rates well beyond what is presently considered practical.

According to the present invention there is provided a method of providing ventilatory assistance to a patient which comprises:

positioning a distal end of a catheter in an area near the carina of a patient; and supplying a continuous supply of an oxygen containing gas mixture to the patient through the catheter.

The present invention further provides a method of providing ventilatory assistance to a patient which comprises continuously flushing anatomical dead space of the patient with a fresh supply of an oxygen containing gas mixture.

Also provided by the present invention is an apparatus for providing ventilation assistance to a patient which comprises a catheter, means for positioning the catheter in an area near the carina of the patient, and means for providing a continuous supply of an oxygen containing gas mixture to the patient through the catheter.

BRIEF DESCRIPTION OF THE DRAWINGS

The present invention will now be described with reference to the annexed drawings, which are given by way of non-limiting examples only in which:

FIG. 2 is a schematic diagram illustrating the catheter utilized in accordance with one embodiment of the present invention.

BEST MODE FOR CARRYING OUT THE INVENTION

Figure 1:
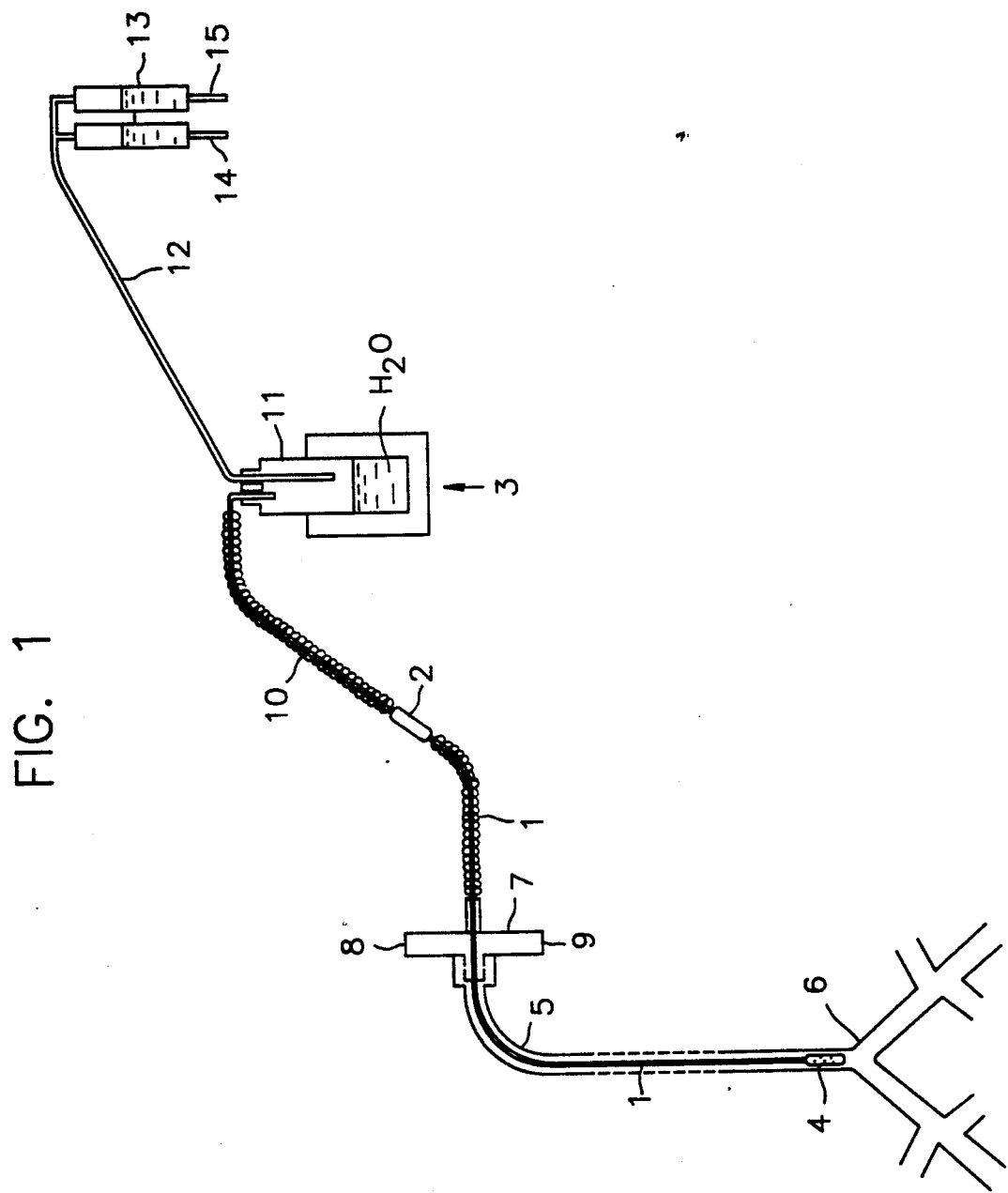
FIG. 1 is a schematic diagram illustrating the ventilation system utilized according to one embodiment of the present invention.

The present invention is directed to a method of intratracheal ventilation (ITV) or intratracheal pulmonary ventilation (ITPV) in which fresh, humidified air/oxygen is introduced at a constant flow rate through a patient's trachea at a position adjacent or near the patient's carina.

In operation, the fresh, humidified air/oxygen is introduced through a very small catheter with a diffuser at its distal end which is placed through an endotracheal or tracheostomy tube, or may be possibly passed percutaneously to rest at the level of the carina. The continuous gas flow is provided at a rate of about 2 to 4 times anatomical dead space per breath. Dead space, as described below, is determined from the volume of the trachea and tracheostomy or endotracheal tube utilized, which, for example in an adult is about 120 cc.

The method of the present invention may be utilized either with or without conventional mechanical ventilation. When utilized without conventional mechanical ventilation, the ITV method of the present invention may be utilized in combination with CPAP. With continuous gas flow, in the constant or continuous positive airway pressure (CPAP) mode the breathing is controlled by the patient. In the ITPV controlled ventilation mode of operation which does not utilize conventional mechanical ventilation, a timed expiratory valve sets the respiratory rate while a minute flow of air/oxygen determines tidal and volume (VT) per breath and hence peak inspiratory pressure (PIP). In this mode the trachea is bypassed, since the fresh air/oxygen is introduced at the patient's carina, and the trachea is therefore used only for expiration. By bypassing the trachea, the anatomical dead space is effectively reduced so that fresh air/oxygen flow rates of approximately 0.5 of the anatomical dead space per breath are acceptable. In the ITPV mode it has been determined that suitable respiratory rates of 10-120 breaths per minute or higher may be used.

When used in conjunction with a conventional mechanical ventilation (MV), the MV is operated in the pressure control mode at low tidal volumes (VT), and hence low peak inspiratory pressure (PIP), with RR adjusted to effect adequate alveolar ventilation.

The method of the present invention effectively eliminates the anatomical dead space ventilation, thereby allowing respiratory rates well beyond what is now considered practical. As an aftereffect, the peak airway pressures remain very low, thus avoiding further harm or aggravation to a patient whose lungs are damaged.

The technique of the present invention is distinct from high frequency ventilation, as tidal volumes remain within the normal range, governed by the compliance of individual lung units; unlike high frequency ventilation/oscillation, with much lower tidal volumes, and very much higher respiratory/oscillatory rates. In laboratory studies, excellent gas exchange was accomplished in lungs as small as 12% of normal volume at very low peak airway pressures.

In studies in healthy animals conducted during the course of the present invention, VT has been reduced as low as 1-2 ml/kg, while PIP at 3-4 cm $H_2O$ above PEEP, at frequencies of 120 breaths per minute. No long term adverse effects resulted utilizing the method/apparatus of the present invention.

The use of ITV alone, or the use of ITV with CPAP, or the use of ITV in combination with a convention MV, greatly facilitates alveolar ventilation both in the low and high frequency range. This mode of ventilation both is distinct from high frequency ventilation, as small or near normal tidal volumes can be used while still effecting excellent CO2 removal.

When the anatomical dead space is continuously flushed with fresh air/oxygen, useful ventilation can be extended to well over 60 breaths per minute. This allows high RR and low VT, and hence low PIP, greatly reducing, or eliminating high airway pressure induced lung injury.

FIG. 1 is a schematic diagram illustrating the ventilation system utilized according to one embodiment of the present invention. As illustrated in FIG. 1, a small catheter I is connected at one end by an adapter 2, e.g., silicone connector, to a means 3 for humidifying and controlling the temperature of an air/oxygen feed.

The distal end of the catheter 1 includes a diffuser 4 which, in use is positioned through a tracheostomy or endotracheal tube 5 to a level adjacent or near a patient's carina 6. The diffuser 4 is preferably formed integral to the distal end of the catheter and is made from suitable material for medical applications, e.g., silicone rubber. Likewise, the catheter is made from suitable material for medical applications, e.g., silicone or teflon. In a preferred embodiment, the diffuser includes a detectable marker or tag such as a radio opaque tantalum marker which may be utilized to assure proper positioning of the diffuser adjacent or near the patient's carina.

As illustrated in FIGS. 1 and 2, the catheter is passed through a conventional fitting 7 which is connected to the tracheostomy or endotracheal tube 5 and includes ports 8 and 9 which may be connected to a mechanical ventilator, including a balloon, and a positive end expiratory pressure regulator, respectively. According to the present invention the fitting 7 is modified as illustrated to allow passage of the catheter 1 through the tracheostomy or endotracheal tube 5.

The means 3 for humidifying and controlling the temperature of an air/oxygen feed is connected to adapter 2 by a sufficient length of tubing 10. In order to ensure that the temperature of the air/oxygen feed is maintained after being adjusted by the means for humidifying and controlling the temperature of an air/oxygen feed, both the tubing 10 and the portion of the catheter which extends from fitting 7 to the tubing 10 are covered or wrapped by a suitable insulating material such as multiple layers of a thin plastic wrap.

The means 3 for humidifying and controlling the temperature of an air/oxygen feed includes a reservoir 11 which is filled with sterile water and heated by a suitable means such as an electrical heater to a temperature of about 37° C. The top of the reservoir 11 is closed by a cover having two ports or fittings to which an air/oxygen supply tubing 12 and tubing member 10 are connected. Air/oxygen is supplied to the air/oxygen supply tubing 12 from a suitable, metered source 13 of air and oxygen which allows for metering of both a source of air 14 and oxygen room temperature.

FIG. 2 is a schematic diagram illustrating the catheter utilized in accordance with one embodiment of the present invention. As illustrated in FIG. 2, the diffuser 4 is preferably formed integral to the distal end of the catheter and includes a plurality of gas passage ports along the length thereof.

In operation, the catheter is passed through the tracheostomy or endotracheal tube 5 so as to position the diffuser 4 at or near the level of the patient's carina. In order to prevent kinking of the catheter, the catheter may be inserted and positioned with the aid of a guide wire.

In operation, the oxygen content of the air/oxygen mixture supplied to the catheter may be adjusted from 21.1 to 100 percent. Thus the mixture may range from pure air to pure oxygen as necessary.

In tests utilizing the system illustrated in FIG. 1, a gas flow rate of about 8.4 liters/minute was provided utilizing a gas flow pressure of about 5 psi; a gas flow rate of about 13.4 liters/minute was provided utilizing a gas flow pressure of about 10 psi; and a gas flow rate of about 17.7 liters/minute was provided utilizing a gas flow pressure of about 15 l psi.

In tests utilizing the system illustrated in FIG. 1, the dead space of the trachea and tracheostomy or endotracheal tube was determined to be about 120 cc. Thus, utilizing a recommended gas flow of 2 times the dead space per breath when used in conjunction with a mechanical ventilator, or while on CPAP, or on spontaneous unassisted ventilation, the following equation was utilized to determine constant gas flow rates at predetermined respiratory rates:

Flow Rate = Respiratory Rate × 2 × Dead Space

From this equation the following flow rates were calculated utilizing the system illustrated in FIG. 1.

| Resiratory Rate (cc per min) | Flow Rate (cc per min) |
|---|---|
| 40 | 9600 |
| 60 | 14400 |
| 80 | 19200 |

When used as ITPV, the required flow rates are greatly reduced, as gas flow remains nearly constant at about 4–5 1/min. at all respiratory rates, the reason being that all fresh gas is delivered bypassing the tracheal dead space.

The following non-limiting examples are presented to illustrate features and characteristics of the present invention which is not to be considered as being limited thereto. In the examples and throughout lung percentages are by volume.

EXAMPLE 1

In a series of young healthy lambs of approximately 10 kg the left lung (total of 43%), plus the right lower and cardiac lobe (81%), plus the right middle lobe (RML)(88%) were progressively excluded from gas exchange. In some tests the lobes were surgically removed; in other tests the bronchi and pulmonary arteries to the respective lobes were tied.

Lambs were sedated and paralyzed. Tests were conducted utilizing a controlled mode MV (Servo 900 C), a tidal volume (VT) not more than 20 ml/kg based on remaining lung mass, a respiratory rate (RR) up to 120 breaths per minute, a PIP of 12–15 cm $H_2O$ and a PEEP of 3 cm H2O.

Those lambs with the right upper lobe (RUL) and RML (19% remaining lungs) were weaned to room air on MV within 48 hours. Ventilating RUL (12% of lung mass) alone required higher VT and PIP to provide adequate alveolar ventilation, but resulted in RDS and death within 8 hours.

EXAMPLE 2

In this example, the ventilation system/method of the present invention was tested for comparison with the results from Example 1 above.

A continuous flow of a humidified mixture of air and oxygen was passed directly into the trachea at the y level of the carina through a diffuser at a rate 4 times the projected tidal volume for the remaining lung, effectively eliminating the tracheal anatomical dead space. A single valve controlled the expiration frequency.

In this example, lambs with only RUL remaining were weaned to room air within 2 hours, at a RR of 60–102 breaths per minute, PIP 14–19 cm $H_2O$, respectively; PEEP 3 cm H20; mean pulmonary artery pressure (MPAP) 30–35 mm Hg. The same lungs subsequently managed on conventional MV at "optimal" settings, following a brief "honeymoon period", progressively deteriorated, and the lambs died after 12 hours from severe RDS. No tracheal lesion were detected in studies lasting up to 3 days.

The ventilation method of the present invention was found to be distinct from high frequency ventilation and its variants, inasmuch as relatively normal tidal volumes are used in proportion to the remaining healthy lung mass. The method of the present invention allows pulmonary ventilation at high rates, with a markedly reduced effective anatomical dead space; it results in normal airway pressures, no evidence of lung injury, and a low MPAP.

It is believed intratracheal ventilation will impact patient management before, and during all stages of current practices in MV.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A method of providing ventilatory assistance to a patient which comprises:
   providing a catheter having a diffuser tip at an end thereof;
   positioning said diffuser tip in an area near the carina of a patient, the patient having an anatomical dead space;
   estimating the anatomical dead space of the patient; and
   simultaneously supplying a constant supply of an oxygen containing gas mixture to the patient through the catheter and diffuser at a flow rate of 0.05 to 4 times the anatomical dead space of the patient per breath and mechanically ventilating the patient at a respiratory rate of 10–120 breaths per minute or higher.

2. A method of providing ventilatory assistance to a patient according to claim 1, comprising the further step of positioning said catheter within said patient by means of an endotracheal tube.

3. A method of providing ventilatory assistance to a patient according to claim 2, comprising the further step of controlling said mechanical ventilation of the patient by means of a timed expiratory valve and using the patient's trachea only for expiration.

4. A method of providing ventilatory assistance to a patient according to claim 1, comprising the further step of positioning said catheter within said patient by means of a tracheostomy tube.

5. A method of providing ventilatory assistance to a patient according to claim 4, comprising the further step of controlling said mechanical ventilation of the patient by means of a timed expiratory valve and using the patient's trachea only for expiration.

6. A method of providing ventilatory assistance to a patient according to claim 1 wherein said flow rate of said oxygen containing gas mixture is 2 to 4 times the anatomical dead space per breath.

7. A method of providing ventilatory assistance to a patient according to claim 1, comprising the further step of positioning said catheter by means of a guide wire.

8. A method of providing ventilatory assistance to a patient according to claim 1, comprising the further step of providing said oxygen containing gas mixture with from 21.1 to 100 vol. % oxygen gas.

9. A method of providing ventilatory assistance to a patient according to claim 1, comprising the further step of humidifying said oxygen containing gas mixture and supplying said oxygen containing gas mixture be a temperature of about 37° C.

10. A method of providing ventilatory assistance to a patient according to claim 1, comprising the further step of performing said mechanical ventilation by means of a timed expiratory valve.

11. An apparatus for providing ventilation assistance to a patient which comprises a fitting, a breathing tube, said fitting connected to said breathing tube and having at least two ports for connecting said fitting to a mechanical ventilator and a pressure regulator, a catheter having a diffuser tip, means for positioning said catheter through said breathing tube for locating diffuser tip an area near the carina of the patient, means for providing a constant supply of an oxygen containing gas mixture to the patient through the catheter at a flow rate of 0.05 to 4 times the anatomical dead space of the patient per breath, and for mechanically ventilating the patient at a respiratory rate of 10–120 breaths per minute or higher.

12. An apparatus for providing ventilation assistance to a patient according to claim 11, further comprising an expiratory valve for principally controlling the patient's expiratory rate.

13. An apparatus for providing ventilation assistance to a patient according to claim 11, wherein said mechanical ventilator comprises a timed expiratory valve.

* * * * *